US008162921B2

(12) United States Patent
Flickinger et al.

(10) Patent No.: US 8,162,921 B2
(45) Date of Patent: Apr. 24, 2012

(54) METHOD AND DEVICE FOR NASAL IRRIGATION AND DRUG DELIVERY

(75) Inventors: William J. Flickinger, Lino Lakes, MN (US); John Quackenbush, St. Paul, MN (US)

(73) Assignee: Medinvent, LLC, White Bear Lake, MN (US)

( * ) Notice: Subject to any disclaimer, the term of this patent is extended or adjusted under 35 U.S.C. 154(b) by 132 days.

(21) Appl. No.: 12/633,269

(22) Filed: Dec. 8, 2009

(65) Prior Publication Data

US 2011/0137290 A1 Jun. 9, 2011

(51) Int. Cl.
*A61M 11/02* (2006.01)

(52) U.S. Cl. .................................. 604/514; 128/200.21

(58) Field of Classification Search .................. 604/514, 604/94.01, 95.01, 95.02; 128/200.21, 203.22
See application file for complete search history.

(56) References Cited

U.S. PATENT DOCUMENTS 2,485,184 A * 10/1949 Blackman et al. ....... 128/200.22
5,624,898 A 4/1997 Frey, II
5,906,198 A * 5/1999 Flickinger ................ 128/200.21
6,313,093 B1 11/2001 Frey, II
6,644,305 B2 * 11/2003 MacRae et al. .......... 128/200.21
7,288,083 B2 * 10/2007 Holman ........................ 604/514
2008/0054099 A1 * 3/2008 Giroux et al. ................ 239/337

OTHER PUBLICATIONS

Ying, "The Nose May Help the Brain: Intranasal Drug Delivery for Treating Neurological Disease"; Future Neural, 2008, 3(1), pp. 1-4.

* cited by examiner

*Primary Examiner* — (Jackie) Tan-Uyen T. Ho
*Assistant Examiner* — Michael J Anderson
(74) *Attorney, Agent, or Firm* — Colin P. Cahoon; Celina M. Orr; Carstens & Cahoon, LLP

(57) ABSTRACT

A method and device for nasal irrigation and drug delivery wherein fluid held in a canister is atomized via a compressed air supply to create particles sized for penetration and retention in the nasal cavity under pressure that is able to stent open the soft tissues of the nose to deliver the resultant mist into the whole of the nasal passages without the need for the patient to create an airstream through inhalation. The device consists of a main canister with a reservoir to hold the fluid, two air outlets and an insert that is placed over the air outlets, the insert having at least one outlet that is larger than the holes in the air outlet and allows the fluid to be atomized and injected directly into the nasal cavity.

20 Claims, 4 Drawing Sheets

304

METHOD AND DEVICE FOR NASAL IRRIGATION AND DRUG DELIVERY

TECHNICAL FIELD

The present invention relates to the delivery of fluid to the upper airway in mist or droplet form, either for the irrigation of the nasal passages or the delivery of medication.

BACKGROUND OF THE INVENTION

Devices used for administering liquid medication to a patient by way of mist or liquid droplets are generally called nebulizers. Typical prior art nebulizers are designed with a single exist port whereby mist or liquid droplets exit the device to be inhaled by the patient. The mist from these nebulizers leaves the device in a low pressure flow rate as a result of baffles or air dams that redirect a venturi jet stream of liquid droplets as the liquid medication is drawn from a liquid reservoir in the device. These devices are best suited for the inhalation of the liquid droplets through the patient's mouth. Certain medical conditions, however, require the introduction of liquid droplets through the patient's nasal passages.

However, current nebulizers, with a single orifice and typically low pressure flow rates, are not effective for introducing liquid medication through the two nostrils of a patient, particularly when the patient's nasal passages are congested or otherwise obstructed. In addition, current nebulizers are designed primarily to deliver particles to the lower airways and require considerable interaction from the patient, including long delivery times.

Therefore, it would be desirable to have a nebulizer that delivers droplets or mists with an air stream and particle size designed to stay in the upper airway, while ensuring that the device fits a wide variety of faces. It would also be desirable to have a nebulizer that allows for simplicity of design and ease of manufacture as well as ease of use, including short delivery times.

SUMMARY OF THE INVENTION

The present invention provides a method and device for nasal irrigation and drug delivery wherein fluid held in a canister is atomized via a compressed air supply to create particles sized for penetration and retention in the nasal cavity under pressure that is able to stent open the soft tissues of the nose to deliver the resultant mist into the whole of the nasal passages without the need for the patient to create an airstream through inhalation. The device consists of a main canister with a reservoir to hold the fluid, two air outlets and an insert that is placed over the air outlets, the insert having at least one outlet that is larger than the holes in the air outlet and allows the fluid to be atomized and injected directly into the nasal cavity.

BRIEF DESCRIPTION OF THE DRAWINGS

The novel features believed characteristic of the invention are set forth in the appended claims. The invention itself, however, as well as mode of use and advantages thereof, will best be understood by reference to the following detailed description of illustrative embodiments when read in conjunction with the accompanying drawings, wherein:

DETAILED DESCRIPTION OF THE DRAWINGS

The present invention improves upon current nebulizer designs and provides a method of delivering fluid to the nasal passages with little interaction required by the user, under sufficient pressure to stent open the airway, and with particles of a size to ensure that the majority of the mist is retained or deposited within the upper airway. The invention also provides a nasal nebulizer designed to deliver a mist to the upper airway through both nostrils simultaneously.

Figure 1:
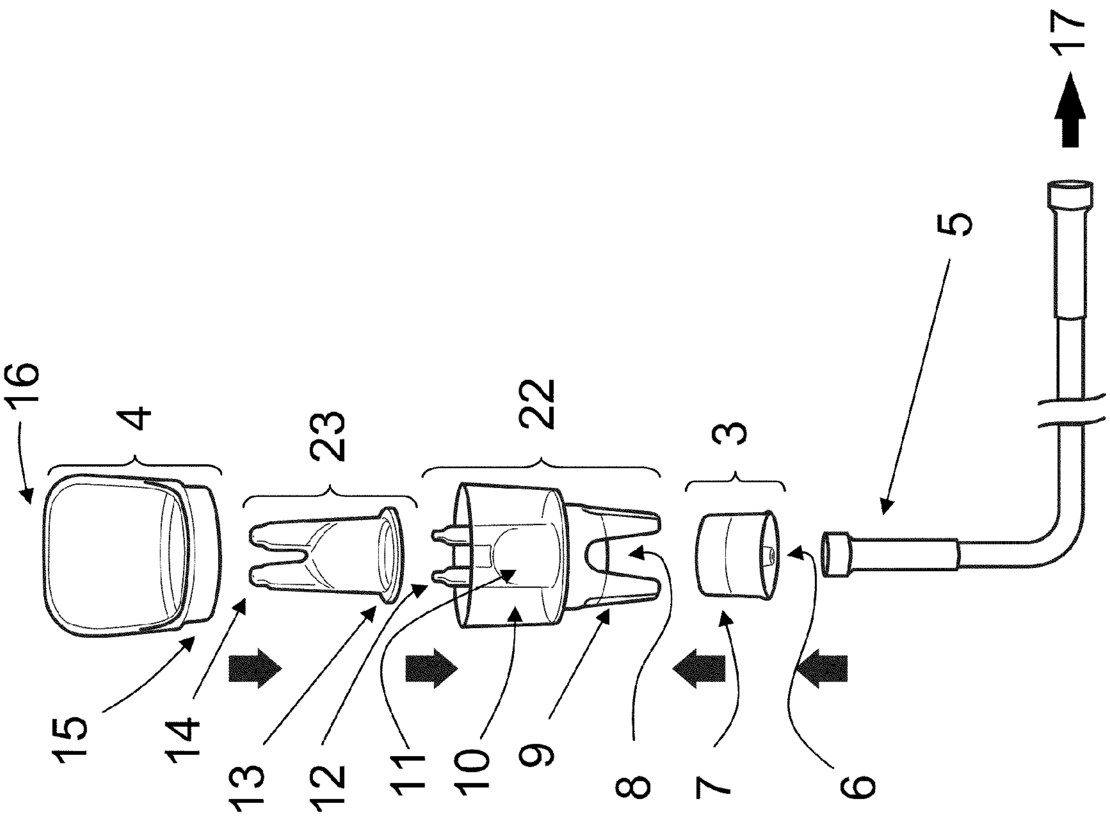
FIG. 1 is an exploded view of a nasal nebulizer in accordance with an embodiment of the present invention.

FIG. 1 is an exploded view of a nasal nebulizer in accordance with an embodiment of the present invention. The nasal irrigation device comprises three major sections. The first major section is the main canister 22 which has an expanded reservoir 10 that is capable of holding up to 50 ml of fluid. The inner portion of the reservoir shaped at the bottom to ensure maximal uptake of fluid to reduce waste.

The main canister 22 also includes an air chamber 11 terminating in two air exits 12 (one for each nostril) with holes sufficient to deliver an airstream that is able to atomize fluid and stent open the upper airway. In one embodiment, each exit port 12 has at least one hole of between 0.020" and 0.060" (0.508 mm-1.524 mm) in diameter and a web-thickness 213 of between 0.030" and 0.060" (0.762 mm-1.524 mm).

On the bottom of the main canister 22 is a foot section 9 that includes one or more feet for stability and an air inlet 8 for the admission of pressurized air to create the air stream through air exits 12. The foot section 9 enables the canister 22 to stand up when set on a horizontal surface and is designed to fit into a standard docking port of an air compressor pump to enable the device to remain upright in a hands-free manner so as to remain filled with the air supply tube attached.

In the shown example, the main canister 22 has a two step diameter to fit a holder (not shown) and provide adequate fluid volume for nasal irrigation, with the smaller diameter foot section 9 enabling the user to rest device in the holder with tube attached. In an alternate embodiment (not shown) the foot section 9 is wider than the reservoir section 10.

The second major section of the nebulizer is the insert 23, which is shown with a base 13 that holds the insert just off of the main canister surface. At least one channel is located in the bottom of the insert 23 to act as a conduit for fluid from the reservoir 10 to enter the base of the insert. The insert 23 includes fluid channels 14 that mate with the air exit ports 12 of the main canister 22. Peaks or extensions on the air exits 12 ensure centering of the insert 23 on the air exits. As shown, fluid channels 14 of the insert 23 comprise two tubes with one end at the bottom of the reservoir 10 and one end that is positioned in the airstream so that the airstream creates a negative pressure in each tube that draws fluid into the airstream where it is atomized (described below).

In the embodiment shown in FIG. 1, the atomizer outlets 12, 14 extend above the edge of the main canister 22. However, in an alternate embodiment (not shown) the atomizer nozzles are even with the edge of the main canister.

The insert 23 is keyed in at least one location with the reservoir 10 to ensure that the insert does not rotate in relation to the exit ports 12 of the main canister. The insert may include a feature to ensure that it is inserted into the main canister in only one orientation. In one embodiment, a loop (not shown) extends down to the saddle of the insert 23 to hold down the insert.

The fluid channels 14 are slightly larger in diameter than the air exit ports 12 of the main canister, thereby providing a small space (preferably 0.0001" to 0.010" (0.00254-0.254 mm)) between the outer surface of the air exit ports and the inner surface of the fluid channels. This space allows fluid from the reservoir 10 to proceed upward between the air exit ports 12 and the fluid channels 14 until being expelled by pressurized air. When the insert 23 is installed in the main canister 22, the orifices of the fluid channels 14 are positioned relative to the air exits 12 so as to create a venturi effect with the pressurized gas expelled from the gas tubes. Because the fluid exits 14 in the insert 23 are larger than the air exits 12, when air is forced through the air exits at an appropriate volume and speed, fluid in the reservoir 10 is drawn up into the space between the insert and air exits ports. When this fluid meets the subsequent airstream it is atomized into particles conducive to deposition in the upper airway. The airstream is sufficient to penetrate the nasal cavity above the inferior turbinate so as to deposit the fluid and provide a washing or irrigation to the upper reaches the nasal cavity.

The exit holes of the fluid channels 14 are small enough to ensure that mist is created but large enough to ensure that the holes of the insert may be chamfered so that the walls of the exit holes are angled away from a central axis at an angle that exceeds the cone of the aerosol plume to reduce agglomeration of the mist particles upon exit, providing a more uniform particle size throughout the plume. The fluid channel size may be adjusted to change the particle size of the mist. In one embodiment the tubes have a mating section on the upper end that enables the changing of the orifice in the air stream via a series of nozzles that can be inserted into the upper end of the tubes such that the size of the nozzle orifice that is placed into the airstream is varied.

The third major section of the nebulizer is nozzle cone 3. The nozzle 3 includes an air inlet 6 and a mating surface 7, which attaches to the air inlet 8 of the main canister 22 to create air chamber 11 defined by the nozzle and the two exit ports 12 described above. The length of all components on the nozzle cone 3 preferably is limited so that the nozzle cone or its components do not extend past the foot section 9 on the main canister 22 when the device is assembled to enable the device to be placed on a flat surface in an upright or standing position.

Ribs may also be molded into the nozzle cone 3 to provide radial stiffness. In another embodiment, the nozzle cone is made of rigid plastic.

The mating surface between the nozzle 3 and main canister 22 is designed to ensure a tight bond can be created. In an alternate embodiment the mating surface between the nozzle 3 and main canister 22 is essentially straight.

In one embodiment, the nozzle cone 3 is attached permanently to the main canister 22. In an alternate embodiment, the nozzle cone 3 may utilize a friction fit or have a positive connection such as a thread or other mechanism allowing the nozzle cone and main canister 22 to be disconnected for cleaning. This detachable embodiment may include an air seal such as an O-ring as well as a flange to grasp for easy disassembly.

An air supply tube 5 connects the air inlet 6 of the nozzle cone with an air supply 17.

Figure 2:
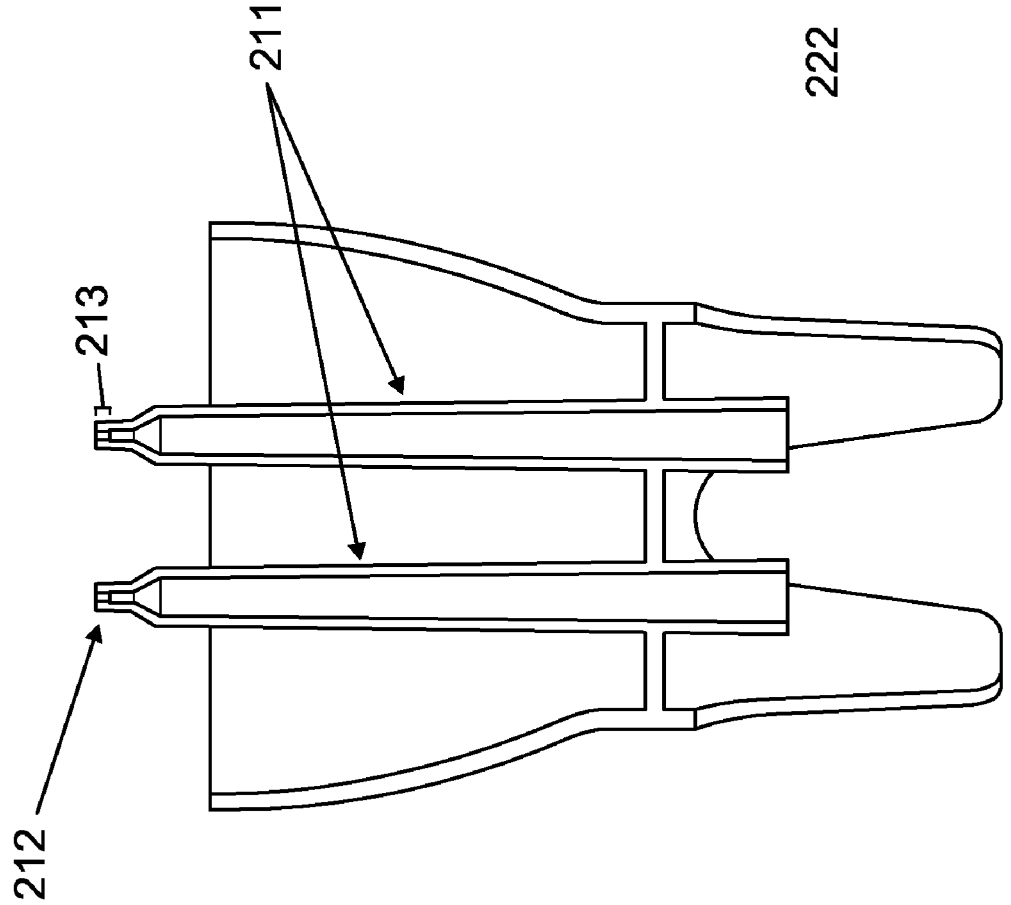
FIG. 2 shows a cross section view of the canister in accordance with an alternate embodiment of the invention.

FIG. 2 shows a cross section view of the canister in accordance with an alternate embodiment of the invention. In this embodiment, rather than a single air chamber and nozzle, the canister 222 includes separate air passage chambers 211 that terminate in the air exits 212. These separate air passage chambers 211 can connect to separate air sources via separate nozzles. Alternatively, the separate air passage chambers 211 can be connected to a common air source via split tubing such as a Y or T adapter (not shown).

In addition to the three major sections described above, the nebulizer may include a cover 4 which has a mating surface 15 that creates an isodiametric connection to the main canister 22. In the example shown in FIG. 1, the cover 4 is a broad cover region to block space between the nose, eyes and the rest of the face when in use as shown (see FIG. 4). In this embodiment the cover 4 is designed to confine the mist expelled from the fluid channels and shield the patient's eyes, with an opening to provide room for the patient's nose within the apparatus. The cover 4 is radiused along the distal end away from the main canister 22 to fit a broad variety of faces and is open to enable air to enter as the fluid is drawn down and capture and recycle fluid that falls off the face.

The cover may also incorporate a cross member or other device that retains the insert 23 to allow for clearance of the nose and prevent lifting of the insert at the initiation of atomization. In one embodiment a sleeve or partial sleeve extends from the cover 4 to the base of the insert 23 to hold the insert down.

Figure 3:
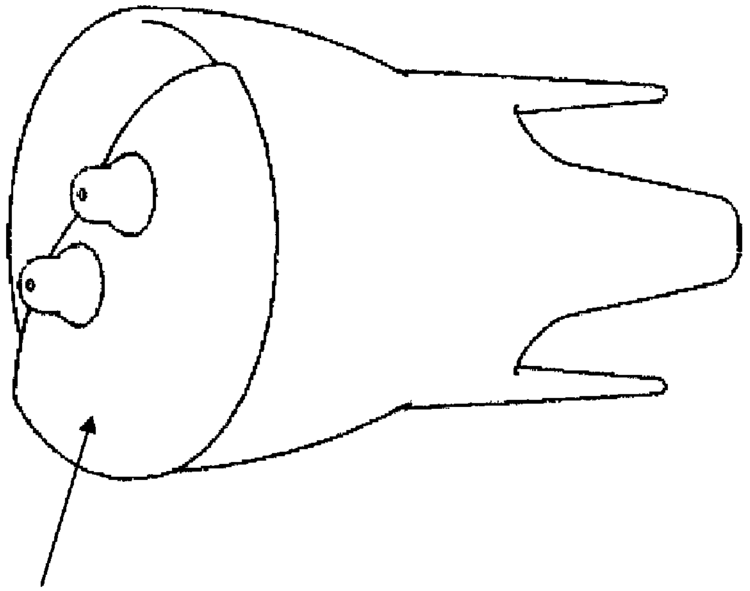
FIG. 3 shows an alternate embodiment of the cover in accordance with the present invention.

FIG. 3 shows an alternate embodiment of the cover in accordance with the present invention. In this embodiment, the cover 304 is a semi-circular lid that does not block the eyes but instead retains the insert and blocks material from reentering the main canister from the nose.

The present invention may incorporate a feature that guides the user to angle the spray into the nose at a set angle from 0-90 degrees from the plane defined as the front of the face from the chin to the forehead (i.e. the vertical plane of the face). For example, the nebulizer may include a setoff designed to set a specific angle of 30 degrees, 45 degrees, or 60 degrees from the vertical plane of the face. The setoff may be removable for various size faces or noses.

Materials suitable for construction of the nebulizer include rigid plastic, glass, metal, ceramic, carbon fiber or other rigid material, or an elastomer plastic or some combination thereof.

One embodiment of the nasal irrigation device (not shown) is egg-shaped or ovoid for better fit into the hand and a pleasing look.

Figure 4:
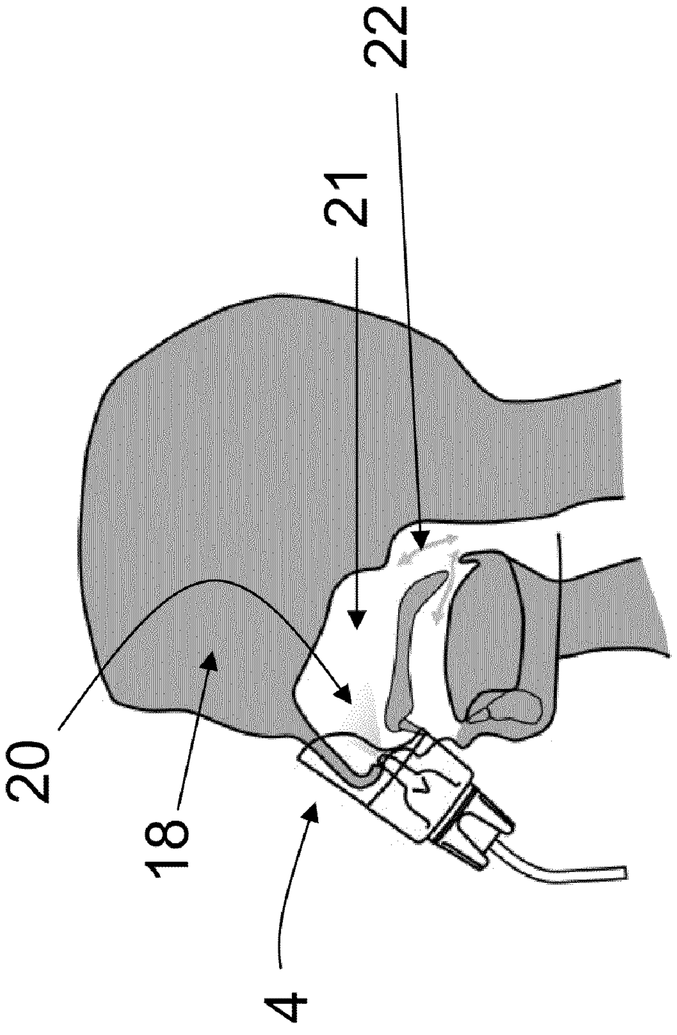
FIG. 4 illustrates the use of the nasal nebulizer in accordance with the present invention.

FIG. 4 illustrates the use of the nasal nebulizer in accordance with the present invention. The nebulizer is placed over the face of the user 18 and angled such that the cover 4 blocks the eyes. The mist 20 enters the nasal passages 21, and the patient breathes through both the mouth and nose at the same time (22). The mist 20 passes into the nasal passages 21 independent of the patient's breathing.

The air-fluid mixture is calibrated to achieve nasal irrigation within a short period of time, without the need for the fluid to exit the nostrils at the time of irrigation, and with a particle size that is designed to loosen the mucous or to enter the sinus cavities, as desired by the end user and not enter the pharynx or the lungs.

The method of nasal irrigation offers a fast, convenient method of atomizing saline or medication for delivery to the nose, with a variable particle size up to 100 microns. In one embodiment, particle size is at least 10 microns.

Using an air pressure of 1-15 psi (0.069-1.035 bar) creates a pressurized airflow that enables the resultant air-mist stream to stent open the soft tissues of the upper airway. Optimal performance appears to occur at 3-12 psi (0.207-0.823 bar), 1-12 lpm of airflow, and a fluid delivery rate of 10-20 ml per minute but will vary according to the needs of the patient.

Typical performance is 4-8 psi (0.276-0.552 bar) pressure, 6-8 lmp airflow, and 15 ml per minute fluid delivery.

The resultant mist reaches the area of the nasal cavity above the inferior nasal turbinate or chonchae to ensure that the mist reaches the areas of the sinus ostia to clear this area of the nasal cavity and enable the natural mucociliary flow to clear the sinuses.

Recent medical research has noted that the olfactory and trigeminal nerves may be used as a pathway to deliver large and small molecules to the brain and central nervous system that bypasses the blood brain barrier and first pass metabolism of intravenous and oral delivery routes. (See Dhanda, D., Frey W H $2^{nd}$, Leopold, D., Kompella, U B: "Nose-to-brain delivery approaches for drug deposition in the human olfactory epithelium." *Drug Delivery Technol.* 5(4), 64-72 (2005).) Frey and others have demonstrated that these nerves may be reached via the nasal mucosa overlying the olfactory cleft and cribriform plate where these nerves are concentrated. Furthermore, the frequency of dosing of many of these materials requires a delivery system that is practical and easy to use. However, the literature suggests that adequate delivery systems are lacking for the reliable and practical delivery of these substances to these areas. Delivery of large particles (>10 microns) of liquids in small volumes, such as provided by the present invention, offers advantages over dry powder and high volume solutions. These advantages include the ability of the liquid to be formulated in such a way as to enable it to remain on the mucosa longer, such as thickening to a gel at body temperature; reducing the inadvertent delivery of aerosolized materials to the lungs; and the ability to deliver precious materials economically and judiciously while reducing waste.

The description of the present invention has been presented for purposes of illustration and description, and is not intended to be exhaustive or limited to the invention in the form disclosed. Many modifications and variations will be apparent to those of ordinary skill in the art. The embodiment was chosen and described in order to best explain the principles of the invention, the practical application, and to enable others of ordinary skill in the art to understand the invention for various embodiments with various modifications as are suited to the particular use contemplated. It will be understood by one of ordinary skill in the art that numerous variations will be possible to the disclosed embodiments without going outside the scope of the invention as disclosed in the claims.

We claim:

1. A nasal nebulizer, comprising:

(a) a main canister with a reservoir for holding fluid, wherein the canister includes at least two air exit ports;

(b) a removable insert with a circular base that fits within said main canister, wherein the insert includes at least two fluid channels that mate with said air exit ports of the main canister, said fluid channels comprising two tubes ending in a common bell housing above the base, wherein said base holds the insert just off of the main canister surface, allowing fluid to pass between the base and main canister, and further wherein the fluid channels are larger in diameter than the air exit ports, thereby providing a small space between the outer surface of the air exit ports and the inner surface of the fluid channels that allows fluid from said reservoir to be drawn upward between the air exit ports and fluid channels and expelled as a mist in an aerosol plume through exit holes in the fluid channels due to a venturi effect created by pressurized air from the air exit ports; and (c) at least one nozzle coupled to the bottom of said main canister to create at least one air chamber defined by the nozzle and said air exit ports, wherein the nozzle includes an air inlet for providing pressurize air into said air chamber.

2. The nasal nebulizer according to claim 1, further comprising a cover coupled to the top of said main canister.

3. The nasal nebulizer according to claim 2, wherein said cover retains the insert inside the main canister, and wherein the cover confines mist expelled from said fluid channels and includes an opening to provide room for a user's nose.

4. The nasal nebulizer according to claim 2, wherein said cover comprises a semi-circular lid that retains the insert and blocks material from re-entering the main canister from a user's nose.

5. The nasal nebulizer according to claim 1, wherein said reservoir in the main canister holds up to 50 ml of fluid, and further wherein said main canister comprises a two step diameter.

6. The nasal nebulizer according to claim 1, wherein each air exit port has at least one hole of 0.508-1.524 mm in diameter.

7. The nasal nebulizer according to claim 1, wherein each air exit port has a web-thickness of 0.762-1.524 mm.

8. The nasal nebulizer according to claim 1, wherein the main canister has a foot section on the bottom that enables the canister to stand upright when set on a horizontal surface.

9. The nasal nebulizer according to claim 7, wherein said foot section fits into a docking port of an air compressor pump, enabling the nebulizer to remain upright in a hands-free manner when the tubing is attached to the air inlet.

10. The nasal nebulizer according to claim 1, wherein the main canister further comprises two separate air passage chambers terminating in said air exit ports, wherein the separate air passage chambers can connect either to separate air sources via separate nozzles or to a common air source via an adapter.

11. The nasal nebulizer according to claim 1, wherein the insert is keyed in at least one location with the reservoir to ensure that the insert does not rotate in relation to the air exit ports of the main canister.

12. The nasal nebulizer according to claim 1, wherein the space between the outer surface of the air exit ports and the inner surface of the fluid channels is 0.00254-0.254 mm.

13. The nasal nebulizer according to claim 1, wherein the size of the fluid channels is adjustable to change the particle size of the mist.

14. The nasal nebulizer in claim 1, wherein the walls of the exit holes in the insert are angled away from a central axis of the holes, such that the angle is greater than that of the aerosol plume, thereby reducing agglomeration of particles on the walls of the holes of the insert and resulting in uniformity of particle size across the resultant aerosol plume.

15. The nasal nebulizer according to claim 1, further comprising a setoff that guides the user to angle the mist into the nose at a set angle of 0-90 degrees from the vertical plane of the face.

16. A method of nasal irrigation, comprising:

(a) providing fluid in a canister that includes at least two air and an insert, said insert comprising a base that fits within the canister;

(b) mating said air exit ports to corresponding fluid channels, wherein the fluid channels wherein the fluid channels comprise two tubes ending in a common bell housing above the base of the insert and are larger in diameter than the air exit ports, thereby providing a small space between the outer surface of the air exit ports and the inner surface of the fluid channels that allows fluid from said reservoir to be drawn upward between the air exit ports and fluid channels; and (c) pumping pressurized air through said air exit ports, thereby creating a venturi effect that draws fluid from said reservoir upward between the air exit ports and fluid channels and expels the fluid as a mist in an aerosol plume through exit holes in the fluid channels and into a user's nasal cavity above the inferior nasal turbinate independent of the user's breathing, said mist comprising a particle size of up to 100 microns and reaching the nasal mucosa overlying the olfactory cleft and cribriform plate to deliver substances to the olfactory and trigeminal nerves, thereby bypassing the blood brain barrier for delivery to the central nervous system;

wherein said pressurize air has a pressure of 0.069-1.035 bar and an airflow rate of 1-12 liters per minute, producing a fluid delivery rate of 10-20 ml per minute.

17. The method according to claim 16, wherein said pressurized air has a pressure of 0.276-0.552 bar.

18. The method according to claim 16, wherein said pressurized air has an airflow rate of 6-8 liters per minute.

19. The method according to claim 16, wherein the fluid delivery rate is 15 ml per minute.

20. The method according to claim 16, wherein the particle size is at least 10 microns.

* * * * *